United States Patent [19]

Homsy

[11] Patent Number: 5,222,985
[45] Date of Patent: Jun. 29, 1993

[54] IMPLANTATION OF ARTICULATING JOINT PROSTHESIS

[76] Inventor: Charles A. Homsy, 11526 Raintree Cir., Houston, Tex. 77024

[21] Appl. No.: 273,145

[22] Filed: Nov. 17, 1988

Related U.S. Application Data

[63] Continuation of Ser. No. 865,336, May 21, 1986, abandoned, which is a continuation of Ser. No. 788,421, Oct. 17, 1985, Pat. No. 4,636,214, which is a continuation of Ser. No. 476,117, Mar. 17, 1983, abandoned, which is a continuation-in-part of Ser. No. 369,731, Apr. 19, 1982, abandoned.

[51] Int. Cl.⁵ ............................................. A61F 2/32
[52] U.S. Cl. ................................................... 623/23
[58] Field of Search .................... 623/16, 18, 20, 22, 623/23

[56] References Cited

U.S. PATENT DOCUMENTS

| | | | |
|---|---|---|---|
| 3,938,198 | 2/1976 | Kahn et al. | 623/23 |
| 3,986,212 | 10/1976 | Sauer | 623/23 |
| 4,153,953 | 5/1974 | Grobbelaar | 623/23 |
| 4,268,920 | 5/1981 | Engelbrecht et al. | 623/18 |
| 4,283,799 | 8/1981 | Pratt, Jr. et al. | 623/20 |
| 4,408,359 | 10/1983 | Burstein et al. | 623/22 |
| 4,454,612 | 6/1984 | McDaniels | 623/23 |

Primary Examiner—David Isabella
Attorney, Agent, or Firm—Bush, Moseley & Riddle

[57] ABSTRACT

An intramedullary prosthesis particularly for a hip prosthesis. The prosthesis utilizes a tapered elongate stem undersized precisely with respect to a precisely formed stem socket in the medullary canal with the stem socket defined by cortical bone or dense cancellous bone of a long bone. A layer of coating material surrounds the undersized stem along its entire length and is of a generally uniform thickness along the entire length of the stem with the costing material filling the void area between the stem of the prosthesis and the precisely formed stem socket.

9 Claims, 3 Drawing Sheets

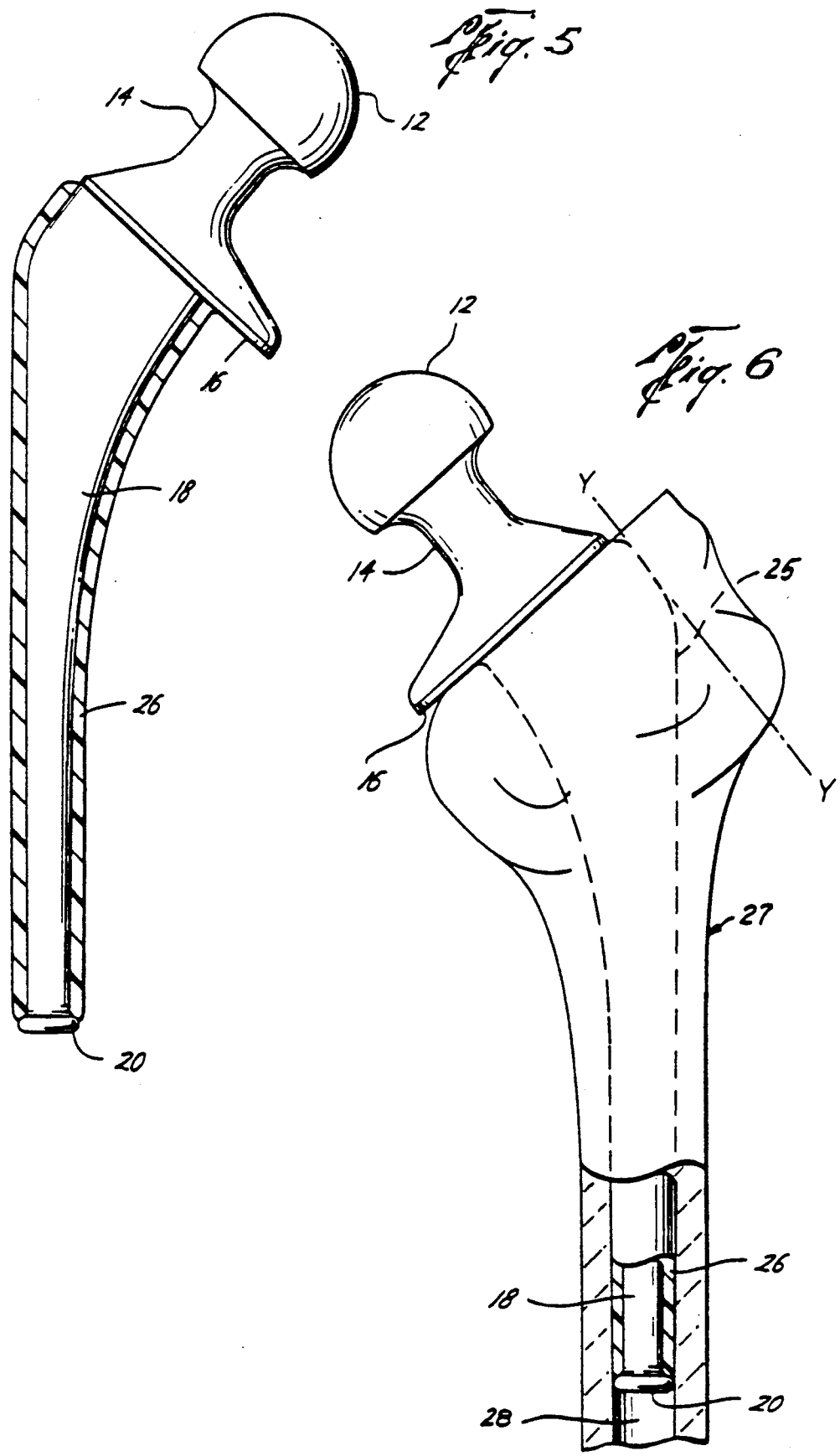

IMPLANTATION OF ARTICULATING JOINT PROSTHESIS

This is a continuation of U.S. patent application Ser. No. 865,336, filed May 21, 1986, now abandoned which is a continuation of application Ser. No. 788,421, filed Oct. 17, 1985, now U.S. Pat. No. 4,636,214; which is a continuation of U.S. patent application Ser. No. 476,117, filed Mar. 17, 1983, now abandoned; which is a continuation-in-part of application Ser. No. 369,731, filed Apr. 19, 1982, now abandoned.

BACKGROUND

This invention relates in general to orthopedic implantation of articulating joint prosthesis of the type known as intramedullary prosthesis or endoprostheses, such as intramedullary hip prostheses.

For many years surgeons have been able to replace the ball of the hip joint with a metal ball. This was done by removing the patient's ball and a part of the neck from the upper end of the femoral bone. A metal prosthesis implant, having a ball, neck, and stem, was then inserted into the medullary canal of the femur. Prior to such insertion, the more centrally-positioned, softer, cancellous bone of the medullary canal had been rasped to form a bone cavity which was able to accept therein the stem of the prosthesis. For convenience, this bone cavity will be called herein a stem socket.

In the known art, the rasps used to form the stem socket were variable in shape and were not precisely correlated with the shape of the desired prosthesis. Transverse sectional dimensions of the stem, at most points along the length thereof, were substantially smaller than the corresponding sectional dimensions of the prepared stem socket. Hence, the stems were generally loosely received within their sockets. Many patients who received such a prosthesis were substantially impaired in their ability to move due to excessive pain and/or to the limited range of articulation of the joint which received the prosthesis.

To better stabilize such stems, they were first provided with transverse holes, and many years later they were provided with pores on their outer surfaces. Bone was expected to grow into the holes and/or pores of the stems. It was hoped that tissue ingrowth would improve the stability of the stems with respect to their sockets.

Because the shapes of the stems with pores were patterned after the shapes of the stems with holes, transverse sectional dimensions of the stems with pores were also, at many points along their length, appreciably undersized with respect to the corresponding sectional dimensions of their stem sockets. It was felt that such stem undersizing was necessary in order not to fracture the femoral bone during insertion of the stem into the prepared stem socket within the medullary canal. Because of such deliberate stem shape undersizing, the known stems lacked the necessary stability when inserted into their sockets and, therefore, could not properly transfer loads to the bone surrounding the stems.

Certain types of articulating joints sustain, in use, high mechanical loads, e.g., hip joints, where stresses occur in the bone which surrounds and defines the medullary canal. Due to poor stem fixations within the medullary canals, many patients who received such undersized stems experienced limited motion due to pain.

Efforts to obtain improved stabilization for such undersized stems lead to the injection of a bone cement paste into the prepared stem socket. The cement cures within and fills the void space between the external surface of the undersized stem and the adjacent tissue. Bone cement became widely used and is now generally accepted as a means for fixing a stem within its socket.

Bone cement typically includes an acrylic polymer powder which is pre-mixed with a compatible liquid acrylic monomer system to produce a doughy paste. The stem is rapidly inserted into the cement paste which then cures or polymerizes into hard cement between the stem and the bone. The hard cement is expected to anchor the stem within the stem socket. Using cement, variations in implantation procedure could be made, such as:

a. changing the manner in which the cement was injected into the prepared stem socket;

b. reducing the viscosity of the cement in order to improve the inter-locking between the cement liner and the porous cancellous bone;

c. lengthening the stem;

d. increasing the medial to lateral dimensions of the stem; and e. eliminating the flange at the prosthesis neck so that only a small portion of the stem's medial and/or lateral outer surfaces at any given longitudinal elevation would impinge against adjacent dense cortical bone during manual insertion of the prosthesis. However, the dimensions of the remaining transverse sections of the stem along its length, above and below such elevation, were still made substantially smaller than the corresponding dimensions of transverse sections of the stem socket. This stem undersizing promoted ease of stem insertion and prevented fracture of the dense femoral cortical bone.

It will be appreciated that cement past allows a surgeon only a very short time interval, typically 5 minutes, within which to fixate the stem within its socket. Subsequently, as the cement polymerizes and hardens, it may shrink leading to the creation of tiny gaps or voids between the cement and the stem on one hand, and/or the cement and adjoining tissue on the other hand. Such voids have been known to adversely affect the ability of the cured hard cement to uniformly transfer load stresses between the stem and the surrounding bone.

But, when the cement non-uniformly transfers such load stresses, there can result a loss of bone starting from the upper end of the femur and leading to a gradual degradation of the useful life of the implantation. In addition, the hard cement itself can be expected to fracture, even as early as 3 to 5 years after surgery. In some extreme cases, cement failure also leads to structural stem fracture. When the cement and/or the stem fractures, the patient suffers great pain, disablement, and requires a new implantation.

A re-implantation of a new prosthesis requires that the old prosthesis be forcefully removed, the hard cement drilled out, and the medullary canal re-reamed, all of which may lead to trauma and dangerous side effects in the patient's body.

Also, the possible migration of unreacted monomer from the bone cement to tissue, and the need for the bone cement to undergo an exothermic polymerization may result in serious damage to tissue surrounding the prosthesis. Such damaged tissue leads to a loosening of the stem within its socket.

Attempts to develop a cementless stem fixation involved using pores on the stem surface, as above mentioned, or adding around the stem a porous outer coating consisting of a ceramic, polymeric, or of a composite of polymer, glass, and/or ceramic. The coated stem was inserted into the stem socket without cement, see for example U.S. Pat. Nos. 3,938,198, 3,986,212, 4,164,794 and 4,307,472.

One known type of porous composite coating, which has the ability to encourage tissue to grow into its pores, is described in "Porous Implant Systems for Prosthesis Stabilization" by C. A. Homsy, et al, Reprint from Clinical Orthopaedics, Nos. 89, Nov.–Dec., 1972, pp. 220–235, and in U.S. Pat. NO. 3,992,725 and foreign patents corresponding thereto. This known coating was bonded to the stems of conventionally-shaped and sized prostheses.

The use of conventionally-shaped prostheses was responsible for many clinical failures. It was discovered that the void space in the stem socket was surrounded substantially by relatively soft cancellous bone which could not sustain the mechanical stress loads imposed thereon. Therefore, the advantages of this known composite coating were not fully utilized until the advent of the present invention.

The success of any implant is typically measured by its ability to assume and carry out the natural functions of the joint in which it is implanted. Thus, an implant must be capable of sustaining the required compressive and flexural stresses imparted to it during normal joint movements.

Prior to this invention, known medullary prosthesis, especially hip joint prosthesis, frequently failed to accommodate normal body functions primarily because the significance and criticality of the transverse sectional dimensions of the stem were not fully appreciated.

The present invention is rooted in the recognition of the importance and criticality of the stem's transverse sectional dimensions, along the entire length thereof, relative to the corresponding transverse sectional dimensions of the medullary canal, as defined by the surrounding dense, cortical bone, known as cortex.

The primary objects of this invention are to provide an improved implantation technique utilizing a novel intramedullary prosthesis characterized by its ability to achieve (1) an adequate initial stabilization within the stem socket, (2) an enduring subsequent stem stabilization, (3) a distributed longitudinal load transfer, (4) an improved load transfer between the stem and surrounding hard cancellous bone and cortical bone, and (5) reduced localized stress zones in the bone opposite to and facing the entire stem.

SUMMARY OF THE INVENTION

Broadly, the improved method of surgical orthopedic implantation of this invention is based on selecting a prosthesis having a stem part which is shaped and sized to correspond substantially to the geometry of the medullary canal in the patient's bone, as defined by the cortical bone or cortex, and then forming a complementary stem socket in the canal which will receive the selected prosthesis.

A preferred aspect to the novel method provides a prosthesis having a stem made of a base material, typically metal, to which is bonded a thin, resilient, compressible, porous coating. The coated stem is oversized along its entire length in relation to the void space in the formed socket. As a result, the stem must be forcibly inserted into the socket. Such forced insertion slightly compresses the coating against the abutting hard bone surrounding and defining the medullary canal. The compressed coating provides a compression fit without appreciably diminishing the coating's porosity. This compression fit extends substantially over the entire length of the stem. The compression fit initially instantly stabilizes the stem within its socket, and subsequently allows tissue to grow into the coating's pores. The initial compression fit and subsequent tissue ingrowth both tend to ensure the stem's long term stability and the stem's load transfer capabilities.

The improved intramedullary prosthesis in accordance with the invention has a stem part whose transverse sectional dimensions substantially approximate the transverse sectional dimensions of the medullary canal, as defined by the cortical bone or cortex, into which it is to be inserted.

In a preferred embodiment, the stem's base material is a suitable metal whose transverse sectional dimensions along its entire length are only slightly undersized relative to the transverse sectional dimensions of the prepared stem socket. The stem's base material is fully covered with a thin coating. The transverse sections of the coated stem part are oversized in relation to the corresponding sections of the prepared socket by an amount ranging from 0.2% to 7%.

By shaping the stem part of the prosthesis to conform substantially to the geometrical shape of the medullary canal defined by the dense cortical bone of the femur, and by bonding to the stem a compressible, porous, resilient coating, it is now possible to obtain, at implantation, a generally uniform press fit between the stem coating and the surrounding hard cancellous bone and cortical bone. Such press fit allows the stem to distribute mechanical loads to the cortical bone, especially in the diaphyseal region, and to the relatively hard cancellous bone and to the cortical bone in the metaphyseal and epiphyseal regions. In addition, the compressed coating also acts as a shock absorber, thereby further improving the long-lasting, post-operative results of the implantation.

When utilizing the method of selecting the shape and size of the prosthesis and of preparing the stem socket in accordance with this invention, significant improvements in stem stabilization and in stem fixation can be obtained, even when using uncoated stems that are to be implanted with the aid of bone cement.

After the proper prosthesis is selected, the medullary canal in the femur is reamed and rasped to form a stem socket having a predetermined shape and length to receive therein either the oversized coated stem alone, or the slightly undersized uncoated stem together with a thin cement layer.

In the case of the coated stem, after preparing the socket, the stem is properly oriented at the mouth of the socket, and with adequate force the stem is gradually pushed into the socket, whereby the resilient, porous coating becomes slightly compressed. At the metaphyseal and epiphyseal levels of the medullary canal, the coating becomes uniformly compressed, whereas at the diaphyseal level of the canal, the medial and lateral surfaces of the coating become predominantly compressed. These compressions, however, are such that the porosity of any portion of the coating is only slightly reduced. The bone tissue will then be in intimate contact with the pores of the compressed coating to allow rapid tissue ingrowth therein.

BRIEF DESCRIPTION OF THE DRAWINGS

FIG. 5 is a side elevation view of a prosthesis according to the preferred aspects of this invention, being a prosthesis substantially as shown in FIG. 1, but with a resilient, porous, tissue-promoting coating thereon.

FIG. 6 is an elevation view of the hip joint prosthesis of FIG. 5 installed in the upper end of a femur with its stem fully extending into the femur's medullary canal.

DESCRIPTION OF THE PREFERRED EMBODIMENTS

With particular reference to the drawings, the prosthesis of this invention, generally designated as 10, has a stem 18 adapted for insertion into the medullary canal 28 (FIG. 6) of a femur 27. Prosthesis 10 is illustrated as being a hip joint prosthesis or femoral ball prosthesis. However, the portion of the description relating to stem 18 and the stem's interrelation with and its fixation within the medullary canal 28 would be equally applicable to other articulating joint prostheses.

Figure 1:
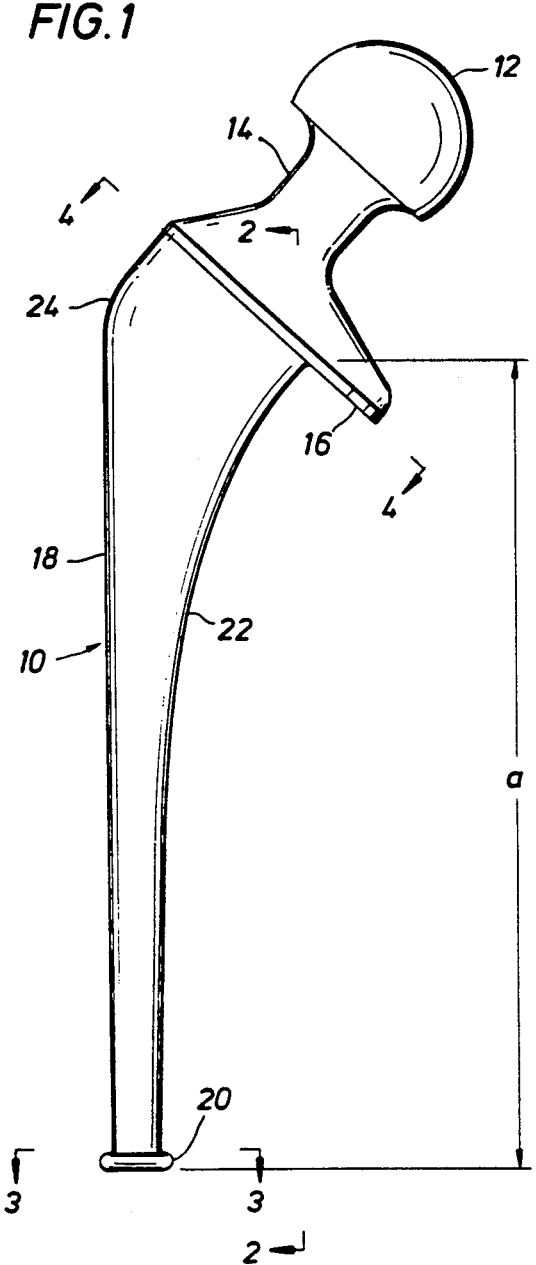
FIG. 1 is a side elevation view of a hip joint prosthesis according to the broad aspect of the present invention.
Figure 2:
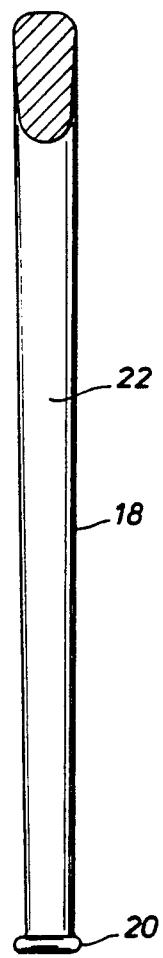
FIG. 2 is a right side elevation of the prosthesis taken along line 2—2 in FIG. 1 with the flange, neck, and ball removed.

With particular reference to FIGS. 1-4, prosthesis 10 includes a ball 12, a flange 16, and a neck 14 which extends therebetween. A stem 18 comprises a shank portion which extends away from the opposite side of flange 16 substantially at a right angle thereto. In side elevation, as shown in FIG. 1, stem 18 is curved at its proximate end and tapers down at its distal end to an annular flange 20.

Figure 3:
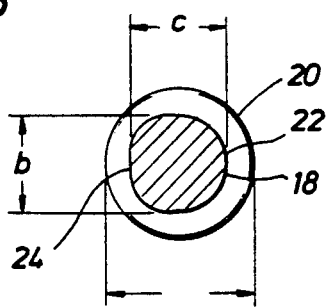
FIG. 3 is a sectional view of the stem, taken along line 3—3 in FIG. 1, showing the flange.
Figure 4:
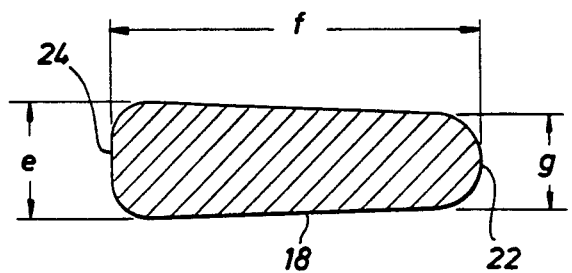
FIG. 4 is a sectional view of the stem taken along line 4—4 in FIG. 1.

Flange 20 is shown as having a circular transverse section and extends radially outwardly by slightly less than 2 millimeters beyond the main body of stem 18. The proximate end of stem 18 is relatively flat and has an inner surface 22 which is rounded and an outer surface 24 which is flat but with rounded edges, as shown in FIGS. 3-4. Instead of having a circular section, flange 20 can have an oval section.

It should be understood that the improved stem 18 should be made in at least three distinct shapes, each shape having a set of distinct dimensions designated in FIGS. 1, 3 and 4 by letters a through g. It has been found in practice that three distinct shapes for a femoral prosthesis will accommodate most shapes of femurs 27 normally encountered in human skeletons. Accordingly, such three distinct shapes for implant 10 can be manufactured in advance and made available to the surgeons, together with instructions for preparing corresponding stem sockets, as will be subsequently described.

The following are dimensions in millimeters for one such shape for a typical small stem prosthesis:

| | |
|---|---|
| a = 139.7 mm | e = 10.0 mm |
| b = 8.2 mm | f = 32.0 mm |
| c = 8.1 mm | g = 8.0 mm |
| d = 12.0 mm | |

In a preferred embodiment, as shown in FIGS. 5-6, a coating 26 of a resilient, porous, tissue-ingrowth-promoting material is bonded to and around stem 18 and completely covers it. No coating is provided around flange 20.

It is preferred that the transverse sections of stem 18 including coating 26 should constitute at least seventy percent (70%) of the corresponding transverse sections of the medullary canal 28 defined by the endosteal or inner contour of dense, hard cortical bone for metaphyseal and epiphyseal segments of a typical long bone of the skeleton, and at least ninety percent (90%) of the corresponding transverse sections of the diaphyseal segment.

Any resilient, tissue-ingrowth-promoting, porous coating 26 may be utilized, so long as it is compatible with the body system of the patient and will bond adequately to the stem's base material which is typically a metal, such as an ASTM F-75 chromium-cobalt-molybdenum orthopedic alloy.

A preferred such coating composition is described in said U.S. Pat. No. 3,992,725, and is sold by Vitek, Inc., Houston, Texas, U.S.A., under the registered trademark PROPLAST.

Briefly, this material, at least in its preferred form, comprises a resilient, fibrous porous structure composed of carbon or graphite fibers, optionally in admixture with a proportion of polytetrafluoroethylene fibers, bonded together with a sintered polytetrafluoroethylene resin.

The porous coating should be bonded at least to substantially the entire surface of the prosthesis that is normally designed for fixation. For example, the stem of a femoral prosthesis would be entirely coated.

It is preferred that coating 26 have a thickness of about 2 millimeters, which is a compromise between several factors including: desired stem strength, coating compression, tissue ingrowth into the coating, and size of the patient's medullary canal. Greater coating compression will lead to a larger porosity reduction.

Before implantation, a stem socket 25 must be prepared in the femur 27. The sectional dimensions of the void space in socket 25 are made such as to obtain at least a one percent and preferably approximately ten percent compression of coating 26, after stem 18 is pushed down to its final seated position in socket 25, as shown in FIG. 6.

Coating 26 is sufficiently porous and sufficiently resilient so that when it becomes partially compressed during the forceful insertion of stem 18 into the preformed stem socket 25, the coating's porosity characteristics and tissue ingrowth capabilities will only be slightly impaired. Coating 26 will also be able to accommodate non-uniformities at least in the upper portion of socket 25, and still achieve a substantially uniform compression fit or interference fit with the abutting hard bone, most cortex.

A proper preparation of socket 25 will take full advantage of the shape of prosthesis 10. For example, outer surface 24 is not covered by flange 16 and extends substantially perpendicularly away from flange 16. Surface 24 curves sharply and then extends in a substantially straight line to bottom flange 20.

With such a geometrical configuration for prosthesis 10, when the lower end of the stem 18 is selected to fit within the prepared socket 25, then coating 26 will be compressed by surrounding bone along substantially the entire length of stem 18.

A combination of specific surgical tools will be used by the surgeon to properly prepare socket 25 for receiving one of the three shapes for the femoral prosthesis 10 provided to the suggestion, as above described.

In general, socket 25 is reamed and rasped into proper shape to allow the oversized coated stem 18 to become inserted therein by the use of force applied to implant 10. As a result, the tissue around the socket's void space will totally surround and make intimate pressure contact with the stem's coating 26 substantially along its entire length.

In particular, with a suitable radiograph, the proper prosthesis shape can be predicted. The instruments subsequently used to develop socket 25 will verify whether the proper shape for prosthesis 10 was predicted with the radiograph.

Standard surgical approaches should be used to expose the patient's hip joint. The approach selected should allow access to the proximal femur along its longitudinal axis. When the hip joint is exposed, dislocation of the femoral head from the acetabulum may be accomplished either with or without a trochanteric osteotomy.

In the following description trochanteric osteotomy is performed along the plane Y—Y shown in FIG. 6, and the trochanter is pivoted away from the neck and ball of the femur.

Using a guide unit, the osteotomy of the femoral neck is performed. The medial level of the osteotomy should be as high as possible above the superior border of the lesser trochanter.

A rongeur is used at the apex of the two osteotomies to develop an entrance cavity for a hand reamer approximately 8 mm in diameter. If the trochanter has not been released, a small drill bit is used to develop the entrance cavity for the hand reamer. The reamer is directed along the long axis of the femur 27 to gain access to the medullary canal 28 through the metaphyseal bone. A guide should be used to direct the location of the tip of the hand reamer or drill bit.

Thereafter, a guide rod of a powered flexible reamer is placed down the longitudinal axis of femur 27 following the cavity developed by the hand reamer or drill bit.

The flexible reamer is used in 0.5 mm size increments to develop the distal end of socket 25 in the diaphyseal segment of the medullary canal. The guide rod previously placed in the canal also acts as a guide for the cannulated cutting heads of the reamer. The reamer cutting heads are increased in size until endosteal cortical bone is touched in the diaphyseal portion of the medullary canal. The size of this reamer indicates and fixes the size of the final reamer used for preparing socket 25 substantially along the longitudinal axis of femur 27. This final reamer size corresponds to a particular prefabricated shape for implant 10, for example, a small prosthesis 10 having the dimensions a-g shown in FIGS. 1, 3 and 4.

As previously mentioned, implant 10 is made in three distinct shapes in order to accommodate most shapes of femurs normally encountered in making femoral implantations.

Using translational motion in line with longitudinal axis of the femur, manual rasping of the developed stem socket with an appropriately sized rasp is carried out. When stem socket 25 is properly sized and shaped, stem 18 is then pushed down into the socket. Because coated stem 18 is oversized by an amount ranging from 0.2% to 7% in its transverse sections as compared to the corresponding transverse sections of its prepared socket 25, it cannot be forced down manually and must be driven in gently with a surgical mallet. Flange 20 serves to protect the leading edge of the coating 26 against abrasion during the forced insertion of coated stem 18 into its socket 25.

Utilizing the foregoing steps, the improved prosthesis 10 of the present invention is implanted with consistent positive results predicated on the implant achieving instant stability in its socket 25. Tissue will start rapidly to grow into the porous coating 26 to ensure proper long-term fixation of the prosthesis.

The soft porous coating 26 will make intimate physical contact with the surrounding bone and prevent abrasion of the cortical bone or of the hard cancellous bone during physical movements of the body subsequent to implantation. Moreover, by virtue of the resiliency of coating 26, a shock gradient is established across the coating that assists in distributing the compressive loads along the implanted stem 18, leading to a longer lasting and more comfortable implant for the patient.

Patients who have received such implants 10 have generally been able to bear with comfort normal weight as early as 3 to 6 weeks after surgery.

Although much less desirable, a similar technique can be employed for the implantation of a prosthesis 10 shaped according to the invention, but not having a resilient, porous, tissue-ingrowth-promoting coating on the base material of stem 18.

The uncoated stem 18 will have to be implanted by the use of a bone cement to form a cement liner around stem 18. The improved load transfer to the cement liner and the support provided to said liner by hard cancellous bone and by hard cortical bone will mediate against premature failure of the cement.

For an uncoated stem 18, bottom flange 20 is either deleted or its outer surface is grooved vertically so that the cement can surround the end of the stem during implantation. The grooved flange 20 would be additionally helpful in centralizing the stem vis-a-vis its surrounding cement liner.

A plug of cement or of plastic is usually positioned distal to the end of the stem to maintain back pressure in the cement during prosthesis emplacement.

Figure 7:
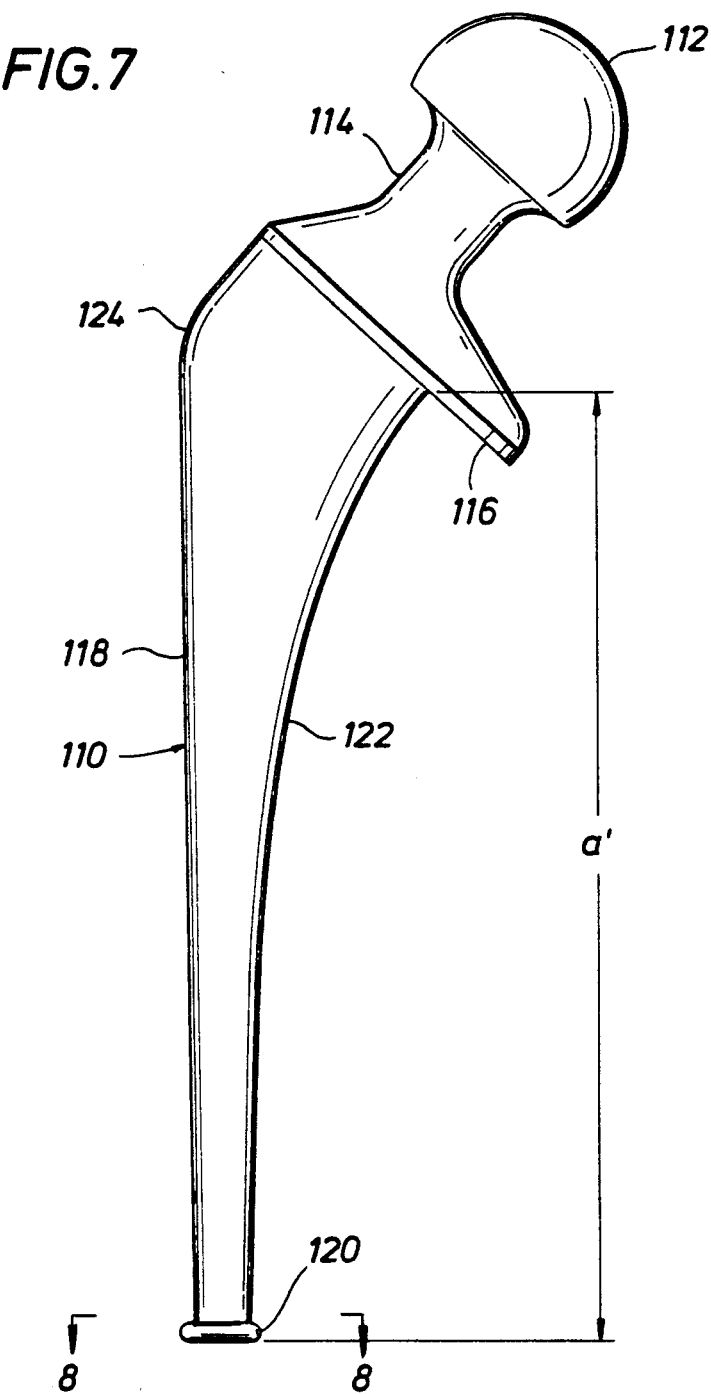
FIG. 7 is a side elevation of a modified hip joint prosthesis.
Figure 8:
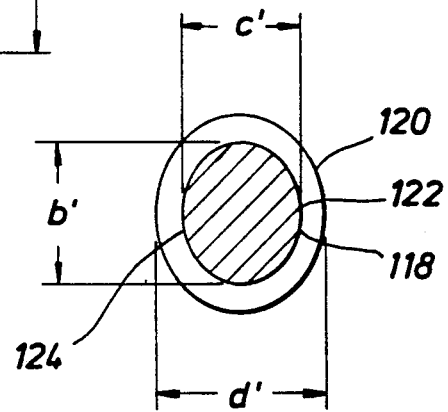
FIG. 8 is a sectional view of the stem taken along line 8—8 in FIG. 7.

As shown in FIGS. 7 and 8 prosthesis 110 has a stem 118 for insertion into a medullary canal. Prosthesis 110 is similar to prosthesis 10 shown in FIGS. 1 to 6 except that the inner one-third portion of stem 118 is generally ovoid in shape having a width in the dimension "b'" which is greater than the breadth dimension "C'". Such change in shape of the inner portion of the stem is provided so that the lower portion of the stem can occupy at least ninety percent (90%) of the transverse sectional opening of the medullary canal opening into which it is inserted. As shown in FIGS. 7 and 8 prosthesis 110 is illustrated to have the same components as prosthesis 10, previously described, with all component numbers having the prefix "1" to indicate they are part of prosthesis 110.

As stated above, while the improved prostheses 10 and 110 of the present invention are illustrated and described with respect to a hip joint prostheses, it will have applications to other articulating joint prostheses, wherein the load transmitted through the joint is conveyed by the implant to the body skeleton by means of a stem or an extension which has to fit within a prepared cavity or socket in the medullary canal portion of the skeleton element in the patient's body.

What is claimed is:

1. An intramedullary prosthesis comprising:

an elongate stem having distal and proximal ends and adapted to be forcibly inserted within an elongated stem socket having its inner periphery defined by compact bone formed by cortical bone or dense cancellous bone of a long bone, said stem having transverse sectional dimensions along substantially its entire length undersized with respect to corresponding transverse sectional dimensions of said socket;

a layer of coating material surrounding said undersized stem along its entire length including its distal and proximal ends and covering substantially the entire outer surface of said stem, the coated stem having transverse sectional dimensions constituting at least around seventy percent (70%) of the transverse sectional dimensions of said medullary canal defined by cortical bone of the metaphyseal and epiphyseal segments of said long bone, and at least around ninety percent (90%) of the corresponding transverse sectional dimensions of the long bone defined by the cortical bone of the diaphyseal segment of said long bone;

said layer of coating material being of a generally uniform predetermined thickness along the entire length of the stem sufficient to provide improved load transfer between the stem and the adjacent compact bone formed by hard cancellous bone and hard cortical bone, said tapered stem being of minimal cross-sectional area adjacent said distal end and of maximum cross-sectional area adjacent said proximal end with said generally uniform thickness coating material progressively increasing in cross-sectional area from said distal end to said proximal end of said stem.

2. The prosthesis as set forth in claim 1 wherein said coating material comprises a soft, resilient material having a relatively low modulus of elasticity generally comparable to the modulus of elasticity of fibrous tissue for being in intimate physical contact with the surrounding bone.

3. The prosthesis as set forth in claim 2 wherein said coated stem is adapted to be oversized in its transverse sectional dimensions with respect to the corresponding transverse sectional dimensions of said socket an amount ranging from two tenths of a percent (0.2%) to around seven percent (7%).

4. The prosthesis as set forth in claim 1 wherein said coating material is bone cement and fills the void between said undersized stem and the inner periphery of the socket formed by said cortical or dense cancellous bone thereby forming a cement liner about the outer periphery of said stem.

5. The prosthesis as set forth in claim 1 wherein the thickness of said coating material relative to the diameter of said stem adjacent said distal end of said stem is of a maximum of around 25% of said diameter, and the diameter of said coating material relative to the minimum sectional dimensions of said stem adjacent said proximal end is of a maximum of around 25% of said minimum sectional dimensions.

6. The prosthesis as set forth in claim 5 wherein the thickness of said coating material is around two millimeters.

7. An intramedullary prosthesis comprising:

a tapered elongate stem having distal and proximal ends and adapted to be forcibly inserted within an elongated socket having its inner periphery defined by cortical bone or dense cancellous bone of a long bone, said tapered stem having transverse dimensions at each point along its length undersized with respect to corresponding transverse sectional dimensions of said socket; and a layer of soft, resilient coating material surrounding said undersized stem along its entire length, said soft coating material being compressible and having transverse outer dimensions along its length oversized with respect to corresponding transverse dimensions of said socket an amount at least around two-tenths of a percent (0.2%) whereby the soft coating material is adapted to be inserted within cortical bone or dense cancellous bone of the socket with an interference fit along its length;

said layer of coating material being of a generally uniform predetermined thickness along the entire length of said stem, said tapered stem being of minimal cross-sectional area adjacent said distal end and of maximum cross-sectional area adjacent said proximal end with said generally uniform thickness coating material progressively increasing in cross-sectional area from said distal end to said proximal end of said stem;

the transverse sectional dimensions of the coated stem constituting at least seventy percent (70%) of the corresponding transverse sectional dimensions of the long bone defined by cortical bone of the metaphyseal and epiphyseal segments of said long bone, and at least ninety percent (90%) of the corresponding transverse sectional dimensions of the long bone defined by the cortical bone of the diaphyseal segment of said long bone;

said soft coating material fitting in intimate physical contact with the surrounding bone and being of a relatively low modulus of elasticity, the softness and resiliency of said coating material along the length of said stem being of a nature as to provide a shock absorber for distributing compressive loads along the length of said stem between the stem and surrounding bone and to minimize abrasion of said cortical bone or hard cancellous bone during and after implantation.

8. The prosthesis as set forth in claim 7 wherein the thickness of said coating material is around two millimeters.

9. The prosthesis as set forth in claim 7 wherein the relatively low modulus of elasticity of said coating material is genrally similar to the modulus of elasticity of fibrous tissue.

* * * * *

REEXAMINATION CERTIFICATE (4186th)

United States Patent [19]
Homsy

[11] B1 5,222,985
[45] Certificate Issued Oct. 24, 2000

[54] IMPLANTATION OF ARTICULATING JOINT PROSTHESIS

[75] Inventor: Charles A. Homsy, Houston, Tex.

[73] Assignee: Tranquil Prospects, Ltd., Road Town, Virgin Islands (Br.)

Reexamination Request:
No. 90/004,640, May 6, 1997

Reexamination Certificate for:
Patent No.: 5,222,985
Issued: Jun. 29, 1993
Appl. No.: 07/273,145
Filed: Nov. 17, 1988

Related U.S. Application Data

[63] Continuation of application No. 06/865,336, May 21, 1986, abandoned, which is a continuation of application No. 06/788,421, Oct. 17, 1985, Pat. No. 4,636,214, which is a continuation of application No. 06/476,117, Mar. 17, 1983, abandoned, which is a continuation-in-part of application No. 06/369,731, Apr. 19, 1982, abandoned.

[51] Int. Cl.[7] .......................................... A61F 2/32
[52] U.S. Cl. .......................................... 623/23.36
[58] Field of Search ................................. 623/16, 18, 20, 623/22, 23, 19, 66

[56] References Cited

U.S. PATENT DOCUMENTS

| | | |
|---|---|---|
| 3,707,006 | 12/1972 | Bokros et al. . |
| 3,740,769 | 6/1973 | Haboush . |
| 3,741,205 | 6/1973 | Markolf et al. . |
| 3,793,650 | 2/1974 | Ling et al. . |
| 3,829,904 | 8/1974 | Ling et al. . |
| 3,843,975 | 10/1974 | Tronzo . |
| 3,852,045 | 12/1974 | Wheeler et al. . |
| 3,875,594 | 4/1975 | Swanson . |
| 3,886,600 | 6/1975 | Kahn et al. . |
| 3,893,196 | 7/1975 | Hochman . |
| 3,905,777 | 9/1975 | Lacroix . |

(List continued on next page.)

FOREIGN PATENT DOCUMENTS

| | | |
|---|---|---|
| 560587 | 10/1923 | France . |
| 2247721 | 4/1974 | Germany . |
| 2444831 | 9/1975 | Germany . |
| 2551013 | 5/1976 | Germany . |
| 2851598 | 11/1978 | Germany . |
| 2744710 | 4/1979 | Germany . |
| 2933237 | 3/1981 | Germany . |
| 762871 | 9/1980 | Russian Federation . |

OTHER PUBLICATIONS

Andriacchi et al., "A Stress Analysis of the Femoral Stem in Total Hip Prostheses", The Journal of Bone and Joint Surgery, Jul. 1976, at 618.

Bryan, William J. et al., "Hip Endoprosthesis Stabilization with a Porous Low Modulus Stem Coating: Factors Influencing Stabilization", Clinical Orthopaedics, Jun. 1982.

Charnley, John, "Low Friction Arthroplasty of the Hip, Theory and Practice", 1979.

Charnley, John, "Anchorage of the Femoral Head Prosthesis to the Shaft of the Femur", The Journal of Bone and Joint Surgery, British Volume, vol. 42–B, 1960, at 28.

DePuy, Canada, Ltd., "Dual Fixation", Orthopedics, Jan. 1980, Feb. 1981, Mar. 1981 ("DePuy Advertisement").

Howmedica International, Inc., "The Exeter Hip System", 1978.

(List continued on next page.)

Primary Examiner—David J Isabella

[57] ABSTRACT

An intramedullary prosthesis particularly for a hip prosthesis. The prosthesis utilizes a tapered elongate stem undersized precisely with respect to a precisely formed stem socket in the medullary canal with the stem socket defined by cortical bone or dense cancellous bone of a long bone. A layer of coating material surrounds the undersized stem along its entire length and is of a generally uniform thickness along the entire length of the stem with the costing material filling the void area between the stem of the prosthesis and the precisely formed stem socket.

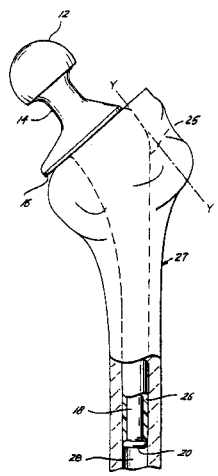

U.S. PATENT DOCUMENTS

| | | |
|---|---|---|
| 3,906,550 | 9/1975 | Rostoker et al. . |
| 3,938,198 | 2/1976 | Kahn et al. . |
| 3,965,490 | 6/1976 | Murray et al. . |
| 3,971,134 | 7/1976 | Bokros . |
| 3,986,212 | 10/1976 | Sauer . |
| 3,992,725 | 11/1976 | Homsy . |
| 4,001,897 | 1/1977 | Rambert et al. . |
| 4,011,602 | 3/1977 | Rybicki et al. . |
| 4,012,796 | 3/1977 | Weisman et al. . |
| 4,021,865 | 5/1977 | Charnley . |
| 4,038,703 | 8/1977 | Bokros . |
| 4,068,324 | 1/1978 | Townley et al. . |
| 4,073,999 | 2/1978 | Bryan et al. . |
| 4,141,088 | 2/1979 | Treace et al. . |
| 4,153,953 | 5/1979 | Grobbelaar . |
| 4,156,943 | 6/1979 | Collier . |
| 4,164,794 | 8/1979 | Spector et al. . |
| 4,245,359 | 1/1981 | Stuhmer . |
| 4,268,920 | 5/1981 | Engelbrecht et al. . |
| 4,280,233 | 7/1981 | Raab . |
| 4,283,799 | 8/1981 | Pratt, Jr. et al. . |
| 4,292,695 | 10/1981 | Koeneman . |
| 4,307,472 | 12/1981 | Morris . |
| 4,314,381 | 2/1982 | Koeneman . |
| 4,351,069 | 9/1982 | Ballintyn et al. . |
| 4,355,428 | 10/1982 | Deloison et al. . |
| 4,365,359 | 12/1982 | Raab . |
| 4,408,359 | 10/1983 | Burnstein et al. . |
| 4,454,612 | 6/1984 | McDaniel et al. . |
| 4,549,319 | 10/1985 | Meyer . |
| 4,770,661 | 9/1988 | Oh . |

OTHER PUBLICATIONS

Miller, Jo, "Improved Fixation in Total Hip Arthroplasty", 1980.

Ranawat, Chitranjan, "DF–80™ System for Total Hip Arthroplasty", 1980, 1982.

Richards Manufacturing Co., Inc., "The Series II", Orthopaedic Review, May 1979, Oct. 1979 ("Richards Advertisement").

Anthony K. Hedley, "Present State, Problems, and Future Implications of Porous–Coated Implants," The Hip (Chapter 16). The Hip Society, p. 329–342, (1980).

Roy Crowninshield, "An Analysis of Femoral Prosthesis Design," The Hip (Chapter 8), The Hip Society, (1981).

Roentgenograms (2) of Anne L. Ridilla (Date Unknown).

Roentgenograms (3) from Rush–Presbyterian Hospital, Chicago, Illinois (Dates unknown but Alleged to be prior to 1980).

Gerarld A. Lord, et al., "An Uncemented Total Hip Replacement," Clinical Orthopaedics and Related Research, No. 141, p. 2–16, (Jun. 1979).

T.M. Wright, et al., "A Method for the Postmortem Evaluation of an in Situ Total Hip Replacement," The Journal of Bone and Joint Surgery, vol. 61A (No. 5), p. 661–668, (Jul. 1979).

Paul M. Pellicci, et al., "Mechanical Failures in Total Hip Replacement Requiring Reoperation," The Journal of Bone and Joint Surgery, vol. 61A (No. 1), p. 28–36, (Jan. 1979).

K.L. Markolf, et al., "A Comparative Experiment Study of Stresses in Femoral Total Hip Replacement Components: The Effects of Prostheses Orientation and Acrylic Fixation," J. Biomechanics, p. 73–79, (1976).

Harlan C. Amstutz, et al., "Loosening of Total Hip Components: Cause and Prevention." The Hip (Chapter 10), The Hip Society, p. 102–116, (1976).

Indong Oh, "Effect of Total Hip Replacement on the Distribution of Stresss in the Proximal Femur: An in Vitro Study Comparing Stress Distribution in the Intact Femur with that after Insertion of Different Femoral Components," The Hip (Chapter 9), The Hip Society, p. 98–123, (1977).

Mark B. Coventry, "Total Hip Relpacement," The Hip (Chapter 4), The Hip Society, p. 68–81, (1980).

R.S.M. Ling, "Total Hip Replacement Using a Collarless Femoral Prosthesis," The Hip (Chapter 5), The Hip Society, p. 82–111, (1980).

William H. Harris, "Total Hip Replacement: Technical Considerations of Femoral Component Insertion," The Hip (Chapter 6), The Hip Society, (1980).

Charles A. Engh, J. Dennis Bobyn, "Biological Fixation of the Porocoat AML Hip," (Date Unknown).

"AML Total Hip," Orthopaedic Nursing, (Date Unknown).

"The Titanium Alloy* Cemented Stem," Ceraver Osteal Advertisement, (1997).

"Loosening of the Femoral Stem Linked to Stem/Canal Size Ratio," Orthopedics Today, (Dec., 1985).

C.A. Homsy, J.N. Kent, E.C. Hinds, "Materials for Oral Implantation–Biological and Functional Criteria," JADA, p. 817–832, (Apr., 1973).

Charles A. Homsy, et al., "Porous Implant Systems for Prosthesis Stabilizaton," Clinical Orthopaedics, p. 220–235, (Nov.–Dec., 1972).

Frederic W. Rhinelander, et al., "Growth of Tissue into a Porous, Low Modulus Coating on Intramedullary Nails: An Experimental Study," Reprinted from Clinical Orthopaedics, p. 293–305, (Apr., 1982– Received Feb. 29, 1980 and presented in part on May 2, 1978 at the Annual Meeting of the Society for Biomaterials) (odd pages only).

Brian Sullivan, et al., "Stabilization of Thompson Femoral Head Prosthesis with a Porous Stem Coating, A Case Report," Reprinted from Clinical Orthopaedics, (May, 1978).

Reference List, Orthapaedic Review, p. 425 (Date Unknown).

Roentgenogram (Aug. 16, 1978).

Roentgenograms (2) of Laura T. Alvignini (Jun. 8, 1079).

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–9 is confirmed.

* * * * *